US006071410A

United States Patent [19]
Nau et al.

[11] Patent Number: 6,071,410
[45] Date of Patent: Jun. 6, 2000

[54] RECOVERY OF ORGANIC SOLUTES FROM AQUEOUS SOLUTIONS

[75] Inventors: David R. Nau, Manhattan Beach; Kevin Gan, Torrance, both of Calif.; Barry C. Arkles, Dresher, Pa.; Guicheng Sheng, Fremont; Hong Zhou, Torrance, both of Calif.

[73] Assignee: Varian, Inc., Palo Alto, Calif.

[21] Appl. No.: 09/192,642

[22] Filed: Nov. 16, 1998

[51] Int. Cl.⁷ .................................................. B01D 15/08
[52] U.S. Cl. ...................... 210/635; 210/656; 210/198.2; 210/502.1; 210/634
[58] Field of Search .................................. 210/635, 634, 210/656, 198.2, 502.1; 502/402

[56] References Cited

U.S. PATENT DOCUMENTS

| | | | |
|---|---|---|---|
| 4,167,551 | 9/1979 | Tamura et al. | 521/27 |
| 4,224,415 | 9/1980 | Meitzner et al. | 521/38 |
| 4,256,840 | 3/1981 | Meitzner et al. | 521/33 |
| 4,297,220 | 10/1981 | Meitzner et al. | 210/690 |
| 4,382,124 | 5/1983 | Meitzner et al. | 521/38 |
| 4,440,905 | 4/1984 | Dunkelberger | 525/66 |
| 4,495,250 | 1/1985 | Itagaki et al. | 428/520 |
| 4,501,826 | 2/1985 | Meitzner et al. | 521/29 |
| 4,539,375 | 9/1985 | Dunkelberger | 525/260 |
| 4,933,372 | 6/1990 | Feilbush et al. | 521/91 |
| 5,322,900 | 6/1994 | Siol | 525/216 |
| 5,446,095 | 8/1995 | Siol | 525/93 |
| 5,773,384 | 6/1998 | Davankov et al. | 502/402 |
| 5,882,521 | 3/1999 | Bouvier | 210/198.2 |
| 5,976,367 | 11/1999 | Bouvier | 210/198.2 |

OTHER PUBLICATIONS

Article by Edouard S.P. Bouvier entitled *"SPE Method Development and Troubleshooting,"* published in *LC–GC* in Nov. 1995, in vol. 13, No. 11, pp. 852, 854, 856, 858.

Chapter 5 by James A. Patterson, entitled *"Preparation of Cross–Linked Polystyrenes and Their Derivatives for Use as Solid Supports or Insoluble Reagents,"* published in *Biochemical Aspects of Reaction on Solid Supports*, Academic Press, New York in 1971, pp. 189–213.

Waters Oasis HLB Extraction Cartridges, Instruction Sheet, P/N WAT058812 Rev 0, 1996 Waters Corporation, pp. 1& 2.

Article by G.I. Rosenberg et al., entitled *"Sorption Properties of Hypercrosslinked Polystryrene Sorbents,"* published in Reactive Polymers in 1983, 1, pp. 175–183.

Article by James S. Fritz et al., entitled *"Method and Materials for Solid–phase Extraction,"* published in *Journal Of Chromatography A*, in 1995, vol. 691, pp. 133–140.

Article by Vadim A. Davankov and Maria P. Tsyurupa, entitled *"Structure and Properties of Porous Hypercrosslinked Polystrene Sorbents'Styrosorb',"* published in *Pure and Appl. Chem.*, in 1989, vol. 61, No. 11, pp. 1881–1888.

Article by Vadim A. Davankov and Maria P. Tsyurupa, entitled *"Structure and Properties of Hypercrosslinked Polystyrene—The First Representative of a New Class of Polymer Networks,"* published in *Reactive Polymers*, in 1990, vol. 13, pp. 27–42.

*Primary Examiner*—Ernest G. Therkorn

[57] ABSTRACT

The present invention provides in one aspect, a novel method for recovering an organic solute from a predominantly aqueous solution. In one embodiment, the solution is contacted with a dry, non-conditioned sorbent medium held by a supporting structure, whereby the solute is absorbed onto the matrix by hydrophobic interactions. A solvent is then passed through the medium, thereby desorbing the solute. Finally, the solute is collected. A further aspect of the invention provides water-wettable sorbent materials for use in solid phase extractions. Embodiments of polymer-based and silica-based sorbent materials are disclosed.

8 Claims, No Drawings

RECOVERY OF ORGANIC SOLUTES FROM AQUEOUS SOLUTIONS

FIELD OF THE INVENTION

The present invention relates to the determination of analytes in fluid samples. In particular, the invention provides for the recovery of organic solutes from predominantly aqueous solutions using non-conditioned chromatographic matrices.

REFERENCES

Bouvier, E. S. P., *LC-GC,* 13(11) (1995) 852, 854, 856, 858.

Davankov et al., U.S. Pat. No. 5,773,384 (1998).

Davankov, et al., *Reactive Polymers,* 13, 27–42, 1990.

Davankov and Tsyurupa, *Pure & Appl. Chem.,* 161, 1881–1888, 1989.

Davankov, et al., SU 299165,1969.

Feibush et al., U.S. Pat. No. 4,933,372 (1990).

Fritz, J. S. et al., *J. Chromatogr. A,* 691 (1995)133–140.

Itagaki et al., U.S. Pat. No. 4,495,250 (1985).

Meitzner et al., U.S. Pat. No. 4,224,415 (1980).

Meitzner et al., U.S. Pat. No. 4,297,220 (1981).

Meitzner et al., U.S. Pat. No. 4,256,840 (1981).

Meitzner et al., U.S. Pat. No. 4,382,124 (1983).

Meitzner et al., U.S. Pat. No. 4,501,826 (1985).

Patterson, J. A., Preparation of crosslinked polystyrene and their derivatives for use as solid support or insoluble reagents, in Biochemical Aspects of Reaction on Solid Supports, Academic Press, New York, 1971, p189.

Rosenberg, et al., *Reactive Polymers,* 1, 175–183, 1983.

Snyder and Kirkland, *Introduction to Modem Liquid Chromatography,* 2nd Edition, (1979) John Wiley and Sons, New York.

Tamura et al., U.S. Pat. No. 4,167,551 (1979).

Waters Oasis HLB Extraction Cartridges, Instruction Sheet," P/N WAT058812 Rev 0,1996, Waters Corporation.

BACKGROUND OF THE INVENTION

Solid Phase Extraction (SPE) has rapidly evolved to become one of the most popular methods for sample preparation. SPE is widely used, for example, to isolate and/or concentrate organic analytes from sample matrices and to provide suitable sample extracts for instrumental analysis. Based on well-known chromatographic principles, SPE is relatively easy to perform and provides superior results compared to traditional liquid—liquid extraction methods.

The term "solid phase extraction" is used because the support material (sorbent bed packing) is a solid, through which a liquid is passed. Typically, a column tube or cartridge, or other support, holds the sorbent bed packing and the liquid phase carries the sample through it. Analytes are adsorbed and eluted according to their differential affinities between the sorbent material and the mobile phase. As the analytes elute, they can be quantified by a detector and/or collected for further analysis.

For the isolation of target compounds bearing non-polar functional groups, a non-polar sorbent is generally employed. According to this technique, referred to as reversed-phase SPE, target compounds are extracted from polar solvents or matrix environments due to hydrophobic interactions between the sorbent and target compounds as they pass through the sorbent bed. Elution of extracted compounds is achieved by organic-based solvents or solvent mixtures having sufficient non-polar character to disrupt the hydrophobic interactions.

In order for the sorbent in a reversed-phase SPE column to retain an analyte, it is necessary for a proper "phase interface" to exist between the sorbent and the sample. To this end, a solvation procedure is usually the first step of an extraction, wherein methanol, acetonitrile, or other organic solvent is passed though the column prior to application of a fluid sample. The solvent "wets" the solid phase, ensuring interaction of the analyte with the sorbent in the following sample application step. For example, with $C_{18}$-bonded silicas, solvation of the hydrocarbon chains allows the hydrophobic ligands to interact properly with organic analytes/solutes present in an aqueous sample. In the absence of such solvation, hydrophobic ligands interact strongly with each other rather than interacting effectively with the organic analytes in aqueous media, often resulting in poor recoveries of the organic analytes.

The general acceptance and perceived importance of sorbent conditioning in the field is underscored by the precautionary statements that users and manufacturers of conventional reversed-phase SPE sorbents often add to the descriptions of their experimental protocols and/or instructions for use. For example:

1. Product Used: Porous styrene-divinylbenzene resin, AMBERCHROM™ 161 (Rohm & Haas Company (Philadelphia, Pa.)) and $C_{18}$-bonded silica (Alltech Associates, Inc. (Deerfield, Ill.)).

Statement: "Chemically bonded silica and porous polystyrene resins have several shortcomings for use in SPE. While silica itself is hydrophilic, the hydrocarbon chains make the surface hydrophobic. The consequence is poor surface contact with predominantly aqueous solutions. Porous polystyrene resins also have a hydrophobic surface. Pretreatment of the SPE materials with an activating solvent (such as methanol, acetone or acetonitrile) must be used to obtain better surface contact with the aqueous solution being extracted."

Reference: p. 136 in "Methods and materials for solid-phase extraction," J. S. Fritz, P. J. Dumont, and L. W. Schmidt, *J. Chromatogr. A,* 691 (1995)133–140.

2. Product Used: $C_{18}$-bonded silicas and hydrophobic polymers in general.

Statement: "Cartridge conditioning is important for reversed-phase sorbents. Wetting the sorbent with an organic solvent such as methanol or acetonitrile will solvate the entire stationary phase and provides the maximum accessible surface for sample adsorption. After conditioning the sorbent with organic solvent, you should keep the bed properly wetted before sample introduction. Premature analyte breakthrough and subsequent variable recoveries can result from improper conditioning or failure to keep the sorbent wetted."

Reference: p.856 in "SPE Method Development and Troubleshooting," E. S. P. Bouvier, *LC-GC,* 13(11) (1995) 852, 854, 856, 858.

3. Product: Waters OASIS™ HLB extraction cartridges (macroporous copolymer [poly(divinylbenzene-co-N-vinylpyrrolidone)] sorbent) (Waters Corporation (Milford, Mass.)).

Instruction: "Solid Phase Extraction Procedure: . . . No step should be omitted . . . 4a. Condition: Add to and draw through each cartridge 1 mL methanol" (emphasis original).

Reference: "Waters Oasis HLB Extraction Cartridges, Instruction Sheet," PIN WAT058812 Rev 0, 1996, Waters Corporation.

Statements and instructions such as these reflect the "conventional wisdom" in the field that SPE sorbent conditioning is necessary in order to obtain acceptable results. In the absence of a conditioning step, it is generally accepted that a reversed-phase sorbent will not be able to properly interact with the organic analytes present in an aqueous sample and, as a result, the analytes will not be effectively retained.

The present invention is based in part on the discovery that certain SPE sorbents provide excellent recoveries for a wide range of organic compounds from aqueous solutions without any conditioning step. It should be appreciated that by eliminating the sorbent-conditioning step, the present invention permits faster and more efficient sample processing. This is significant since sample preparation is widely regarded as the primary bottleneck in the analysis of small organic compounds in aqueous fluids (e.g., drugs in biofluids).

SUMMARY OF THE INVENTION

One aspect of the present invention provides a method for recovering an organic solute from a predominantly aqueous solution using a dry, non-conditioned sorbent medium held by a supporting structure.

In one embodiment, the solution is contacted with the dry, non-conditioned sorbent medium, whereby the solute is absorbed onto the matrix, e.g., due to hydrophobic interactions. The medium, in this embodiment, is a blend of (i) a polymethacrylate resin and (ii) a polystyrene resin. A solvent or solvent mixture is passed through the medium, thereby desorbing the solute, and the solute is collected from the medium.

According to one particular embodiment, the polymethacrylate component of the medium has the following physical properties:

a particle size of about 20–200 μm, and preferably about 50–100 μm;

a surface area of about 300–1,000 m$^2$/g, and preferably about 450–650 m$^2$/g;

a pore size range of about 10–800 Å, and preferably about 10–500 Å; and a pore volume of about 1.0–1.5 ml/g, and preferably about 1.15–1.20 ml/g.

According to a further embodiment, the polystyrene component of the medium has the following physical properties:

a particle size of about 20–200 μm, and preferably about 75–150 μm;

a surface area of about 300–1,000 m$^2$/g, and preferably about 450–550 m$^2$/g;

a pore size range of about 10–800 Å, and preferably about 300–600 Å; and a pore volume of about 1.0–1.5 ml/g, and preferably about 1.25–1.35 ml/g.

In one embodiment, the dry-weight ratio of (i):(ii) is from about 20:1 to about 1:20. In an exemplary mixture, the dry-weight ratio of (i):(ii) is about 2:1.

According to one embodiment, the solute is a compound of less than about 20,000 Daltons. Exemplary solutes include drugs, pesticides, herbicides, biomolecules, toxins, pollutants, or metabolites or degradation products thereof.

Exemplary solutions include blood plasma, serum, urine, cerebrospinal fluid, synovial fluid, tissue extracts, groundwater, surface water, soil extracts, food substances, or extracts of food substances.

In accordance with another embodiment of the present invention, the sorbent medium is an inorganic solid phase, e.g., silica, bearing alkyl urethane surface groups. Similar to the previous embodiment, a predominantly aqueous solution containing an organic solute of interest is contacted with the dry, non-conditioned sorbent medium. A solvent or solvent mixture is passed through the medium, thereby desorbing the solute, and the solute is collected from the medium.

In one embodiment, the alkyl urethane has the formula:

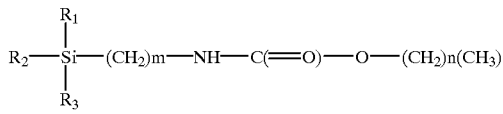

wherein $R_1$ is an alkyl group having from 1 to 6 carbons, an alkoxy group having from 1 to 6 carbons, or a halogen group;

$R_2$ is an alkyl group having from 1 to 6 carbons, an alkoxy group having from 1 to 6 carbons, or a halogen group;

$R_3$ is an alkyl group having from 1 to 6 carbons, an alkoxy group having from 1 to 6 carbons, or a halogen group;

m is an integer of from 1 to 8; and n is an integer of from 0 to 17.

According to one preferred embodiment, the alkyl urethane has the formula:

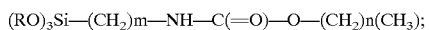

wherein R is an alkyl of from 1 to 6 carbons; m is an integer of from 1 to 8; and n is an integer of from 0 to 17. In a related embodiment, the alkyl urethane has the formula:

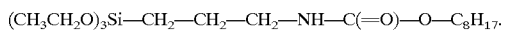

In one embodiment, the alkyl urethane is bonded covalently to silica particles.

Similar to the previous embodiment, one embodiment contemplates the recovery of a compound of less than about 20,000 Daltons. Such a solute can be, for example, a drug, pesticide, herbicide, biomolecule, toxin, pollutant or a metabolite or degradation product thereof.

Also similar to the previous embodiment, the solution can be, for example, blood plasma, serum, urine, cerebrospinal fluid, synovial fluid, a tissue extract, groundwater, surface water, a soil extract, a food substance, or an extract of a food substance.

In another of its aspects, the present invention provides a water-wettable, reversed-phase sorbent medium.

According to one embodiment, the medium comprises a mixture of (i) a polymethacrylate resin, and (ii) a polystyrene resin.

The dry-weight ratio of (i):(ii) can be, for example, from about 20:1 to about 1:20. In one embodiment, the dry-weight ratio of (i):(ii) is from about 3:1 to about 1:1. One preferred mixture contemplates a dry-weight ratio of (i):(ii) of about 2:1.

In one particular embodiment, the polymethacrylate component of the medium has the following physical properties:

a particle size of about 50–100 μm;

a surface area of about 450–650 m$^2$/g;

a pore size range of about 10–500 Å; and a pore volume of about 1.15–1.20 ml/g.

In another particular embodiment, the polystyrene component of the medium has the following physical properties:

a particle size of about 75–150 μm;

a surface area of about 450–550 m$^2$/g;

a pore size range of about 300–600 Å; and a pore volume of about 1.25–1.35 ml/g.

In a related embodiment, the polystyrene component of the medium includes divinylbenzene as a cross-linker.

Another aspect of the present invention provides a water-wettable, reversed-phase sorbent medium comprising an alkyl urethane having the formula:

$$(RO)_3Si—(CH_2)m—NH—C(=O)—O—(CH_2)n(CH_3);$$

wherein R is an alkyl of from 1 to 6 carbons; m is an integer of from 1 to 8; and n is an integer of from 0 to 17. An inorganic solid support is bonded covalently to the alkyl urethane.

In one embodiment, the alkyl urethane has the formula:

$$(CH_3CH_2O)_3Si—CH_2—CH_2—CH_2—NH—C(=O)—O—C_8H_{17}.$$

According to another embodiment, the inorganic solid support is silica.

Yet a further aspect of the present invention provides a novel silane.

In one embodiment, the silane of the invention has the formula:

$$(RO)_3Si—(CH_2)_m—NH—C(=O)—O—(CH_2)_n(CH_3);$$

wherein R is an alkyl of from 1 to 6 carbons; m is an integer of from 1 to 8; and n is an integer of from 0 to 17.

In one particular embodiment, the silane has the formula:

$$(CH_3CH_2O)_3Si—CH_2—CH_2—CH_2—NH—C(=O)—O—C_8H_{17}.$$

These and other features and advantages of the present invention will become clear from the following description.

DETAILED DESCRIPTION OF THE INVENTION

The following discussion of the preferred embodiments of the present invention is merely exemplary in nature. Accordingly, this discussion is in no way intended to limit the scope of the invention, application of the invention, or the uses of the invention.

The present invention provides for the recovery of organic solutes from predominantly aqueous solutions using non-conditioned, chromatographic matrices.

Generally, according to one aspect of the invention, a predominantly aqueous solution containing a solute of interest is contacted with a non-conditioned (dry), reversed-phase sorbent bed. Upon flowing the solution through the bed, the organic solute is separated from other components of the solution. An appropriate solvent can be passed through the sorbent bed to elute the organic solute. Upon exiting the bed, the organic solute can be collected.

As previously mentioned, conventional wisdom in the field dictates that reversed-phase sorbents must be conditioned with an organic-based solvent prior to applying an aqueous sample in order to achieve acceptable results. Contrary to this widely accepted notion, a further aspect of the present invention provides several reversed-phase sorbent materials that provide excellent recoveries for a wide range of water-soluble organic compounds without the need for any conditioning step.

Generally, the sorbent materials provided herein are of two categories: (i) polymer-based and (ii) those based on an inorganic support material. More particularly, the sorbent materials include moieties or entities that are partially water-soluble and hydrophilic, as well as moieties or entities that are hydrophobic enough to bind polar organic compounds and other analytes of interest that may be present in predominantly aqueous samples. Without committing to any particular theory, it is believed that the hydrophilic portion of the sorbent keeps the entire sorbent solubilized, thereby obviating the need for a conditioning step and ensuring sufficient sorbent-solute interaction upon application of an aqueous sample.

With regard to the polymer-based materials, the present invention provides a novel polymer mixture, or blend, prepared from a methacrylic ester-based polymeric resin and a polystyrene-based resin.

In one embodiment, the methacrylic ester-based polymeric resin takes the form of highly-crosslinked polymethacrylate particles of the general formula (Formula I) and physical properties (Table I):

Formula I:

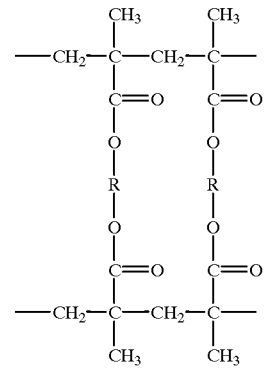

TABLE I

| General Properties of Preferred Polymethacrylate Resins | |
| --- | --- |
| Particle Size | 50–100 μm |
| Surface Area | 450–650 m²/g |
| Pore Size Range | 10–500 Å |
| Average Pore Size | 200–300 Å |
| CephC Capacity | 25–30 mg/ml |
| Pore Volume | 1.15–1.20 ml/g |
| Skeletal Density | 1.25–1.30 g/ml |
| Exclusion Limit | 150–200 kDa |

Guidance for preparing resin particles from methacrylic acid ester monomers can be found, for example, in U.S. Pat. Nos. 4,501,826; 4,382,124; 4,297,220; 4,256,840; 4,224,415; 4,933,372; each of which is expressly incorporated herein by reference.

A preferred methacrylic ester-based polymeric resin for use in the mixture is AMBERCHROM CG-71m (Trademark of Rohm & Haas Company (Philadelphia, Pa.)), commercially available from TosoHaas (Montgomeryville, Pa.).

Further in this embodiment, the polystyrene-based polymeric resin is a macroporous styrenic-based polymeric bead-type resin. The polystyrene resin can include divinylbenzene as a cross-linker. Certain exemplary polystyrene resins, contemplated by one particular embodiment of the invention, are characterized by the following physical properties:

TABLE II

General Properties of Preferred Polystyrene Resins

| | |
|---|---|
| Particle Size | 75–150 μm |
| Surface Area | 450–550 m²/g |
| Pore Size Range | 300–600 Å |
| CephC Capacity | 35–45 mg/ml |
| Pore Volume | 1.25–1.35 ml/g |
| True Wet Density | 1.00–1.03 g/ml |

Guidance for preparing polystyrene-based resin particles can be found, for example, in U.S. Pat. Nos 4,167,551, 4,495,250, and 5,773,384; each of which is expressly incorporated herein by reference; as well as in: Davankov, et al., SU 299165, 1969; Rosenberg, et al., *Reactive Polymers,* 1, 175–183, 1983; Davankov and Tsyurupa, *Pure & Appl. Chem.,* 161, 1881–1888,1989; Davankov, et al., Reactive Polymers, 13, 2742, 1990 (and references therein); and J. A. Patterson, Preparation of crosslinked polystyrene and their derivatives for use as solid support or insoluble reagents, in Biochemical Aspects of Reaction on Solid Supports, Academic Press, New York, 1971, p189; also expressly incorporated by reference.

A preferred polystyrene-based polymeric resin for use in the mixture is DIAION® HP20SS (Trademark of Mitsubishi Kasei Kabushiki Kaisha (Tokyo, Japan), commercially available from Mitsubishi Kasei America, Inc. (White Plains, N.Y.).

Generally, the two polymeric resins are mixed in a ratio (dry weight) of about 20:1 to 1:20, polymethacrylate:polystyrene. In one embodiment, the dry-weight ratio is about 3:1 to about 1:1, polymethacrylate resin to polystyrene resin; and preferably about 2:1. The mixture can be suspended in a suitable liquid medium, e.g., an alcohol, and blended (stirred) for several hours. The mixture is then collected, e.g., by filtration, and dried.

Now with regard to inorganic support materials, inorganic support materials useful in practicing the present invention can include, for example, fiberglass, glass spheres, silica, alumina, titanium dioxide, clays, metals and metallic oxides carrying lipophilic organic surface groups. Surface groups can be applied to the inorganic support by coating or by covalent attachment. The silica, or other support, in this case acts primarly as a carrier for the organic surface groups.

In one embodiment, the inorganic support is comprised of silica particles. The silica can be of a wide range of grades. The silica can be of any suitable shape, such as regular, irregular, spherical, etc. In this embodiment, preferred particle sizes range from about 3 μm to about 500 μm. Further in this embodiment, preferred pore sizes range from about 50 Angstroms to about 1500 Angstroms. One particularly preferred type of silica, useful for the silica-based sorbents of the present invention, is available commercially as GRADE 633 NAT from W. R. Grace & Co. (Baltimore, Md.).

In one embodiment, the inorganic sorbent is a silylcarbamate, having both a hydrophobic moiety and a hydrophilic moiety, immobilized on a silica carrier. Preferably, a carbamate group (hydrophilic moiety) is attached to a silica particle through the nitrogen atom of the carbamate group, and an alkyl or other lipophilic group (hydrophobic moiety) is attached to the oxygen atom of the carbamate. Exemplary carbamates are alkyl (e.g., ethyl, octyl, etc.) carbamate and pyrrolidinone carbamate.

In one exemplary embodiment, the ligand (for attachment to an inorganic support) is an alkyl urethane having the formula:

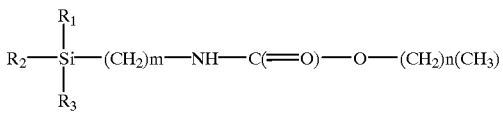

wherein
$R_1$, $R_2$, and $R_3$ are, separately, an alkyl group having from 1 to 6 carbons, an alkoxy group having from 1 to 6 carbons, or a halogen group;
m is an integer of from 1 to 8; and
n is an integer of from 0 to 17.

For example, the alkyl urethane can be a trichlorosilane, a dialkylmonoalkoxysilane, a dialkylmonochlorosilane or a trialkoxysilane, among others.

According to one preferred embodiment, the ligand is an O-alkyl-N-trialkoxyalkylsilane. Such compounds can be prepared by conventional synthesis methods, as described in Example 3.

A newly synthesized alkyl urethane that performs exceptionally well in the method of the present invention is O-octyl-N-triethoxypropylsilane, shown in Formula II:

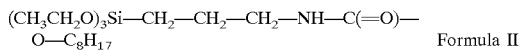
Formula II

One exemplary method for preparing the compound of Formula II is described in Example 2.

The novel sorbent materials of the present invention are particularly useful in solid phase extractions.

In practice, the solution contacted with the sorbent material is predominantly aqueous in nature (i.e., greater than about 50% water by volume). For example, the solution can comprise water, or a mixture of water and a water-miscible organic solvent. Alternatively, the solution can comprise a mixture of water or an aqueous buffer and a polar, water-miscible organic solvent.

The predominantly aqueous solution can include a single type of solute or a plurality of solutes. In one embodiment, a solution containing a complex variety of solutes is applied to the sorbent bed. Solutions of this type include blood plasma, serum, urine, cerebrospinal fluid, synovial fluid and other biological fluids, including extracts of tissues, such as liver tissue, muscle tissue, brain tissue and heart tissue. Such extracts can be aqueous extracts or organic extracts that have been dried and subsequently reconstituted in water or in a aqeous-organic mixture.

The solution can also be ground water, surface water, drinking water or an aqueous or organic extract of an environmental sample, such as a soil sample. The solution can further be a food substance or an aqueous or aqueous-organic extract thereof.

Extraction media of the present invention are particularly useful in recovering polar and/or semi-polar, organic-based solutes from solutions. The solute should be of polarity suitable for adsorption onto the sorbent material. A variety of compounds can be efficiently removed, concentrated, and/or isolated from an extensive range of biological matrices using the teachings of the present invention. Typical extractions include (i) pharmaceuticals from plasma or urine, (ii) pesticides, herbicides, toxins and environmental pollutants from water, (iii) peptides from plasma, and (iv) drugs of abuse from urine or serum. The solutes can also be metabolites or degradation products of the foregoing materials. The solutes can also include biomolecules, such as proteins, peptides, hormones, polynucleotides, vitamins, cofactors, metabolites, lipids and carbohydrates.

The solution can be contacted with the reversed-phase sorbent in any fashion that permits intimate contact of the sorbent and the solution, such as a batch or chromatographic process. For example, the solution can be forced through a sorbent bed such as a column, disk, strip or plug, or the solution can be stirred with the sorbent particles, such as in a batch-stirred reactor. The solution can also be added to a sorbent-containing well of a microtiter plate.

The solution is contacted with the sorbent for a time period sufficient for the solute of interest to substantially adsorb onto the sorbent material. This is typically the time necessary for the solute to equilibrate between the sorbent surface and the solution. The adsorption or partition of the solute onto the sorbent material can be partial or complete.

The reversed-phase sorbent material can be of any suitable form. In one embodiment, the sorbent is packed as particles within an open-ended container to form a solid phase extraction cartridge. The container can be, for example, a cylindrical container or column which is open at both ends so that the solution can enter the container through one end, contact the sorbent bed within the container, and exit the container through the other end. For example, the sorbent can be packed within the container as small particles, e.g., beads and/or pellets, having a diameter between about 5 $\mu$m and about 500 $\mu$m; and preferably between about 20 $\mu$m and about 200 $\mu$m. Alternatively, the sorbent particles can be packed in the container enmeshed in a porous membrane (e.g., a membrane disk or strip).

The container can be formed of any material that is compatible, within the time frame of the extraction process, with the solutions and solvents to be used in the procedure. Such materials include glass and various plastics, such as high-density polyethylene and polypropylene. In one embodiment, the container is cylindrical through most of its length and has a narrow tip at one end (e.g., a syringe barrel).

The solid phase extraction cartridge can further comprise a porous retaining means, such as a filter element, or frit, at one or both ends of the cartridge adjacent to the sorbent bed to retain the sorbent bed within the cartridge and to remove undissolved solid materials from the solution as it flows into the cartridge, while still permitting solution flow into and out of the cartridge. Such a filter can be formed from, for example, fritted glass or a porous polymer, such as a porous high-density polyethylene.

The cartridge can be a single use cartridge, which is used for the treatment of a single sample and then discarded, or it can be used to treat multiple samples.

In an alternative embodiment, the sorbent bed is a monolithic matrix formed in, or inserted into, an appropriate supporting structure, such as a column tube, cartridge, microplate well, or channel of a microdevice.

The amount of sorbent material suitable for a given extraction depends upon the amount of solute to be adsorbed, the available surface area of the sorbent material and the strength of the interaction between the solute and the sorbent material. This can be readily determined by one of ordinary skill in the art.

The sorbents described herein can all be used in relatively simple, user friendly and generalized methods, including the steps of:

1) sample application (without conditioning/pretreatment);
2) a wash with water or a mixture of water with low content of organic solvent (e.g., 5% methanol in water); and 3) organic solvent elution.

In a typical purification protocol, the solution to be treated is added to the top of a solid phase extraction cartridge and allowed to flow through the cartridge, bringing the solute to be adsorbed into contact with the dry, non-conditioned sorbent material. In one embodiment, the solution is allowed to flow through the cartridge under the force of gravity. In another embodiment, an increased flow rate is achieved by establishing a pressure difference between the ends of the cartridge. Such a pressure difference can be established by attaching a vacuum source to the lower end of the cartridge or by applying positive pressure to the upper end of the cartridge. For example, a pressurized gas, such as air or nitrogen, can be applied to the top of the cartridge, or the air within the cartridge above the sorbent bed can be compressed with a piston or plunger. The flow rate of the solution through the cartridge can be adjusted by regulating the pressure difference across the cartridge. Suitable solution flow rates, given in terms of the linear velocity of the solution, range up to about 14 mm/second, but are preferably in the range from about 0.7 to about 3.5 mm/second.

Solvents that are suitable for desorbing the solute from the sorbent material will typically be polar water-miscible organic solvents, for example, methanol, ethanol, isopropanol, acetonitrile, acetone, and tetrahydrofuran, or mixtures of water and these solvents. The desorbing solvent can also be a nonpolar or moderately polar water-immiscible solvent such as dichloromethane, diethylether, chloroform, or ethylacetate. Mixtures of these solvents are also suitable. Typically, preferred solvents or solvent mixtures must be determined on a case-by-case basis. A suitable solvent can be determined by one of ordinary skill in the art without undue experimentation, as is routinely done in chromatographic methods development (Snyder and Kirkland, *Introduction to Modern Liquid Chromatography*, 2nd Edition, (1979) John Wiley and Sons, New York). Either isocratic or gradient elution may be used.

The methods of the present invention can be used to prepare solutions of a solute which are suitable for quantitative analysis via a variety of techniques, including high performance liquid chromatography, liquid chromatography/mass spectrometry, gas chromatography, gas chromatography/mass spectrometry, and immunoassay, among other analytical techniques. Several exemplary extractions are described next.

In one embodiment, the solute is of a polarity suitable for adsorption onto the sorbent bed. The method comprises contacting a first solution that includes the solute with a dry, non-conditioned sorbent bed, whereby the solute is adsorbed onto the sorbent material. This is followed by washing the sorbent bed with a suitable, stronger solvent or mixture of solvents, thereby desorbing or eluting the solute from the sorbent bed and forming a second solution that contains the solute. This second solution is suitable for the quantitative analysis of the solute.

The solution contacted with the dry, non-conditioned sorbent bed can comprise the solute of interest in dilute form, for example, at a concentration too low for accurate quantitation. By adsorbing the solute onto the sorbent bed and then desorbing the solute with a substantially smaller volume of a less polar solvent, a solution which includes the solute of interest can be prepared having a substantially higher concentration of the solute of interest than that of the original solution. The method also results in solvent exchange, that is, the solute is removed from a first solvent and re-dissolved in a second solvent.

The solution contacted with the sorbent bed can comprise a polar solvent and is preferably predominately, i.e. greater than 50% by volume, an acidic, basic or neutral aqueous solution or aqueous buffer. The solution can also comprise a water-miscible polar organic solvent such as methanol, ethanol, acetonitrile, N,N-dimethylformamide, or dimethylsulfoxide, or a mixture of such a solvent and water.

The solution comprising the solute of interest can further comprise one or more additional solutes. In one embodiment, the additional solute or solutes are more polar than the solute of interest, and, thus, adsorb more weakly to the sorbent bed than the solute of interest. Such an additional solute can be desorbed from the sorbent bed by washing the sorbent bed with a solvent which does not desorb the compound of interest, thereby forming a solution of the additional solute or solutes which is substantially free of the solute of interest. A suitable solvent for the desorption of the additional solute will typically be sufficiently polar that it does not desorb the compound of interest. After desorption of the additional solute or solutes, the compound of interest can be desorbed by washing the polymer with a suitable, less polar, solvent. This forms a solution of the organic solute which is substantially free from more polar solutes and is suitable for the quantitative analysis of the organic solute.

In one embodiment, the solute of interest adsorbs onto the sorbent bed, but one or more additional solutes do not. Such an additional solute can be, for example, of sufficiently high polarity that it does not adsorb onto the sorbent bed. The additional solute can also comprise large molecules, for example, macromolecules such as proteins, which are unable to pass through small pores within the sorbent bed, and, thus, have access to only a small fraction of the overall surface area of the sorbent bed material. Such molecules are typically retained poorly, if at all, by the sorbent bed.

In a further embodiment, the additional solute or solutes are less polar than the solute of interest and, thus, adsorb to the sorbent bed more strongly than the compound of interest. The compound of interest can be weakly to moderately adsorbed or not adsorbed. If adsorbed, the solute of interest is desorbed from the sorbent bed by washing the bed with a solvent of sufficient polarity that it does not desorb the additional solute or solutes. Thus, the compound of interest can be desorbed from the sorbent bed without desorbing the other solutes.

In one embodiment, the additional solute or solutes are also analytes of interest. Thus a series of solutes initially present in a solution can be separated, and solutions of each suitable for quantitative analysis can be formed using the method of the present invention. In this case, the solution is contacted with the non-conditioned, dry sorbent bed so that the solutes are adsorbed. The solutes are then desorbed from the sorbent bed in order of decreasing polarity (i.e., most polar solute first, followed by solutes of successively decreasing polarity) by washing the bed with a sequence of solvents of decreasing polarity.

The methods of the invention can be performed on an analytical scale or in large-scale applications.

Objects and advantages of this invention are further illustrated by the following examples, but the particular materials and amounts thereof recited in these examples, as well as other conditions and details, should not be construed to unduly limit this invention.

EXAMPLE 1

Preparation of Polymer Blend Sorbent

A polymer sorbent was prepared using (i) a polymethacrylate resin and (ii) a polystyrene resin (with divinylbenzene cross-linker), according to the following procedure:

100 g pre-washed & dried polymethacrylate resin (Amberchom CG-71 m, TosoHaas) and 50 g pre-washed & dried polystyrene resin (HP20SS, Mitsubishi Kasei America, Inc.) were added to a three-neck round bottomed flask equipped with a drying tube and a mechanical stirrer. To this mixture, 500 mL of methanol was added. The suspension was stirred for four hours and filtered through a filtration funnel. The filter cake was allowed to dry in air for four hours before being transferred to a beaker. The mixed polymer was then oven dried at 70 degrees C under vacuum for 18 hours.

EXAMPLE 2

Preparation of O-Octyl-N-triethoxypropylsilane Sorbent

An inorganic sorbent was prepared using (i) octylurethane silane and (ii) silica, according to the following procedure:

A. Preparation of Silane

A three-neck round-bottomed flask, equipped with an overhead stirrer, a refluxing condenser and a drying tube, was charged with 3-isocyanatopropyltriethoxysilane (12.4 gram, Gelest, Inc.) and toluene (150 mL, Aldrich). Stirring was started, and n-octanol (7.2 gram, Aldrich) was added to the flask. The mixture was stirred and heated to 50 degrees C for 18 hours.

B. Bonding of the Silane to Silica

A three-neck flask, equipped with an overhead stirrer, a reflux condenser and a drying tube, was charged with the solution of octylurethane silane in toluene (above) and silica (20 grams, Grace 633NAT) which had been dried overnight at 160 degrees C. The mixture was stirred and heated to reflux for 24 hours. The mixture was then cooled and filtered. The filter cake was washed three times with methanol and three times with acetone and dried.

EXAMPLE 3

Preparation of O-alkyl-N-trialkoxyalkysilanes

O-alkyl-N-trialkoxyalkylsilanes can be prepared, for example, in accordance with the following exemplary methods:

Method A: Treatment of $O=N-(CH_2)_m-Si(OR)_3$ [where, e.g., m is an integer of from 1 to 8; and R is an alkyl of from 1 to 6 carbon atoms] with an appropriate alkyl alcohol, $CH_3(CH_2)_n-OH$ [where, e.g., n is an integer of from 0 to 17], similar to the procedure of Example 2.

Method B: Treatment of an appropriate alkyl alcohol, $CH_3(CH_2)_n-OH$ [where, e.g., n is an integer of from 0 to 17], with trichloroethyl chloroformate, $CCl_3CH_2O-C(=O)-Cl$. The adduct is subsequently treated with $NH_2-(CH_2)_m-Si(OR)_3$ [where, e.g., m is an integer of from 1 to 8; and R is an alkyl of from 1 to 6 carbon atoms] with heating.

Method C: Treatment of an appropriate alkyl alcohol, $CH_3(CH_2)_n-OH$ [where, e.g., n is an integer of from 0 to 17], with phosgene, then the adduct is treated with $NH_2-(CH_2)_m-Si(OR)_3$ [where, e.g., m is an integer of from 1 to 8; and R is an alkyl of from 1 to 6 carbon atoms].

Method D: Treatment of ethyl or methyl chloroformate with $CH_2=CH-(CH_2)_m-NH_2$ [where, e.g., m is an integer of from 1 to 8]. The adduct is then treated with an appropriate alkyl alcohol, $CH_3(CH_2)_n-OH$ [where, e.g., n is an integer of from 0 to 17], in the presence of acid catalyst. The alkene urethane is then hydrosilated with $HSi(OR)_3$

[where, e.g., R is an alkyl of from 1 to 6 carbon atoms] with heavy metal catalyst to give the target compound.

EXAMPLE 4

Comparative Recovery Data

Data of this example show increased recoveries of exemplary solutes (drugs) in a solid phase extraction application using the non-conditioned sorbent materials of the present invention (Polymer mixture, Octylurethane) compared to columns using non-conditioned conventional polymers or bonded silica particulates (Amberchrom, HP20ss, $C_{18}$).

TABLE III

Recoveries of Organic Compounds on Different Sorbents by SPE Extractions

| Sorbents | Polymer Mixture | Amberchrom | HP20SS | Octylurethane | $C_{18}$ |
|---|---|---|---|---|---|
| Carbamezapine | 99% | 100% | 14% | 100% | 65% |
| Nordiazepam | 83% | 100% | 9% | 99% | 63% |
| Diazepam | 94% | 88% | 15% | 100% | 63% |
| Benzoic acid | 86% | 56% | 52% | 24% | 50% |
| Trimethoprime | 94% | 24% | 15% | 84% | 17% |
| Prednisolone | 73% | 41% | 47% | 100% | 1% |
| Propanolol | 96% | 24% | 16% | 28% | 16% |
| Bethametasone | 86% | 26% | 21% | 100% | 31% |
| Testosterone | 58% | 30% | 26% | 89% | 76% |
| Average Recovery: | 85.4 | 54.3 | 23.9 | 80.4 | 42.4 |

Protocol for SPE Extractions of this Example:

| | |
|---|---|
| Sorbent: | Non-conditioned, Sorbent mass: 30 mg for polymers, 200 mg for silica-based |
| Application: | 1 mL of serum spiked with drugs |
| Washing: | 1 mL of water |
| Elution: | 1 mL of MeOH |
| Analysis: | HPLC with UV detection |

It is evident that, relative to conventional $C_{18}$ products and most commercially available polymers that do not retain analytes in the absence of a conditioning step, the materials and methods of the present invention provide excellent recoveries for aqueous samples applied directly to a dry sorbent bed. For example, compounds with non-polar functional groups (e.g., aromatic rings, alkyl chains) are extracted from polar solutions using non-polar sorbents, without the necessity of preconditioning the sorbents.

It should be appreciated that the present invention represents a significant breakthrough in the field of chromatography since these sorbents eliminate the need for any pretreatment step thereby reducing analysis time, labor and solvent usage, and increasing throughput and productivity.

Those skilled in the art can now appreciate from the foregoing description that the broad teachings of the present invention can be implemented in a variety of forms. Therefore, while this invention has been described in connection with particular embodiments and examples thereof, the true scope of the invention should not be so limited. Various changes and modification may be made without departing from the scope of the invention, as defined by the appended claims.

It is claimed:

1. A method for recovering an organic solute from a predominantly aqueous solution using a dry, non-conditioned sorbent medium held by a supporting structure, comprising:

contacting the solution with the dry, non-conditioned sorbent medium, wherein the medium is a blend of (i) a polymethacrylate resin and (ii) a polystyrene resin, whereby the solute is absorbed onto the matrix;

flowing a solvent or solvent mixture through the medium, thereby desorbing the solute; and collecting the solute from the medium.

2. The method of claim 1, wherein said polymethacrylate has the following physical properties:

a particle size of about 20–200 μm;

a surface area of about 300–1,000 $m^2/g$;

a pore size range of about 10–800 Å; and a pore volume of about 1.0–1.5 ml/g.

3. The method of claim 1, wherein said polystyrene has the following physical properties:

a particle size of about 20–200 μm;

a surface area of about 300–1,000 $m^2/g$;

a pore size range of about 10–800 Å; and a pore volume of about 1.0–1.5 ml/g.

4. The method of claim 1, wherein the dry-weight ratio of (i):(ii) is from about 20:1 to about 1:20.

5. The method of claim 4, wherein the dry-weight ratio of (i):(ii) is about 2:1.

6. The method of claim 1, wherein the solute is a compound of less than about 20,000 Daltons.

7. The method of claim 6, wherein the solute is a drug, pesticide, herbicide, biomolecule, toxin, pollutant or a metabolite or degradation product thereof.

8. The method of claim 6, wherein the solution is blood plasma, serum, urine, cerebrospinal fluid, synovial fluid, a tissue extract, groundwater, surface water, a soil extract, a food substance, or an extract of a food substance.

* * * * *